United States Patent
Bingel et al.

(10) Patent No.: US 6,984,743 B1
(45) Date of Patent: Jan. 10, 2006

(54) METHOD FOR PRODUCING METALLOCENES

(75) Inventors: Carsten Bingel, Kriftel (DE); Berthold Schiemenz, Frankfurt (DE); Markus Göres, Eschborn (DE)

(73) Assignee: Basell Polyolefine GmbH, Wesseling (DE)

( * ) Notice: Subject to any disclaimer, the term of this patent is extended or adjusted under 35 U.S.C. 154(b) by 418 days.

(21) Appl. No.: 09/508,057

(22) PCT Filed: Sep. 3, 1998

(86) PCT No.: PCT/EP98/05588

§ 371 (c)(1),
(2), (4) Date: Mar. 7, 2000

(87) PCT Pub. No.: WO99/12943

PCT Pub. Date: Mar. 18, 1999

(30) Foreign Application Priority Data

Sep. 11, 1997 (DE) ................................ 197 39 946

(51) Int. Cl.
*C07F 17/00* (2006.01)
*B01J 31/00* (2006.01)
*C08F 4/44* (2006.01)

(52) U.S. Cl. ............................ 556/11; 556/12; 556/43; 556/53; 556/58; 534/11; 534/15; 526/160; 526/943; 502/103; 502/117

(58) Field of Classification Search ................. 556/11, 556/12, 43, 53, 58; 526/160, 943; 502/103, 502/117; 534/11, 15
See application file for complete search history.

(56) References Cited

U.S. PATENT DOCUMENTS

| | | | |
|---|---|---|---|
| 4,752,597 A | 6/1988 | Turner | 502/104 |
| 5,017,714 A | 5/1991 | Welborn, Jr. | 556/12 |
| 5,103,030 A | 4/1992 | Rohrmann et al. | 556/12 |
| 5,264,590 A | 11/1993 | Strickler | 549/208 |
| 5,302,733 A | 4/1994 | Diefenbach | 556/11 |
| 5,304,614 A | 4/1994 | Winter et al. | 526/127 |
| 5,543,535 A | 8/1996 | Lisowsky | 556/11 |
| 5,597,935 A | 1/1997 | Jordan et al. | 556/11 |
| 5,612,462 A | 3/1997 | Lisowsky | 534/15 |
| 6,015,916 A * | 1/2000 | Sullivan et al. | 556/7 |

FOREIGN PATENT DOCUMENTS

| | | |
|---|---|---|
| EP | 129 368 | 12/1984 |
| EP | 320 762 | 6/1989 |
| EP | 416 815 | 3/1991 |
| EP | 537 686 | 4/1993 |
| EP | 669 340 | 8/1995 |

OTHER PUBLICATIONS

Chem. Rev. 1992, 92, 965-994, Halterman.
Agnew.Chem.107, 1255-1283, Brintzinger et al. (1995).
J.Org.Chem., 232(1982)233-247, Wild et al.
Org. 1966,15,4030-4037, Diamond et al.
Chem. Abst. 57032b (vol. 121, Aug. 19, 1994).
Chem.Abst. 163528p (vol. 120, Mar. 1994).

* cited by examiner

*Primary Examiner*—Porfirio Nazario-Gonzalez
(74) *Attorney, Agent, or Firm*—Novak Druce & Quigg; Jason D. Voight

(57) ABSTRACT

The present invention relates to a process for preparing a metallocene, which comprises reacting a ligand starting compound with an adduct of the formula (I), $$M^1X_nD_a \qquad (I)$$

where $M^1$ is a metal of group III, IV, V or VI of the Periodic Table of the Elements or an element of the lanthanide or actinide series, preferably titanium, zirconium or hafnium, particularly preferably zirconium, X are identical or different and are each halogen, $C_1-C_{10}$-alkoxy, $C_6-C_{10}$-aryloxy, $C_1-C_{10}$-alkylsulfonate such as mesylate, triflate, nonaflate, $C_6-C_{10}$-arylsulfonate such as tosylate, benzenesulfonate, $C_1-C_{10}$-alkylcarboxylate such as acetate, formate, oxalate or 1,3-dicarbonylate such as acetylacetonate or fluorinated 1,3-dicarbonylate, in particular chlorine, bromine, particularly preferably chlorine, n is an integer and is 2,3,4,5 or 6 and corresponds to the oxidation number of the metal $M^1$, a is an integer or fraction and $0<a\leq 4$ and a is preferably in the range from 0.5 to 2.5 and is in particular 1, 1.5 or 2, and D is a linear, cyclic or branched oligoether or polyether containing at least two oxygen atoms or an oligothioether or polythioether containing at least two sulfur atoms.

10 Claims, No Drawings

METHOD FOR PRODUCING METALLOCENES

The present invention relates to a process for preparing metallocenes.

Metallocenes can be used, if desired in combination with one or more cocatalysts, as catalyst components for the polymerization and copolymerization of olefins. In particular, halogen-containing metallocenes are used as catalyst precursors which can, for example, be converted by means of an aluminoxane into a polymerization-active cationic metallocene complex (EP-A-129368).

Metallocenes are not only of great interest for the polymerization of olefins, but they can also be used as hydrogenation, epoxidation, isomerization and C-C-coupling catalysts (Chem. Rev., 92 (1992), 965–994).

The preparation of metallocenes is known per se (U.S. Pat. No. 4,752,597; U.S. Pat. No. 5,017,714; EP-A-320762; EP-A-416815; EP-A-537686; EP-A-669340; H. H. Britzinger et al., Angew. Chem., 107 (1995), 1255; H. H. Britzinger et al., J. Organomet. Chem. 232 (1982), 233). For this purpose, for example, cyclopentadienyl-metal compounds can be reacted with halides of transition metals such as titanium, zirconium, hafnium, vanadium, niobium, tantalum, chromium, molybdenum, cerium, thorium or uranium. It is also known from the literature that metallocenes can be obtained, for example, by reaction of cyclopentadienes with amides of group IV of the Periodic Table of the Elements (U.S. Pat. No. 5,597,935; R. F. Jordan et al., Organometallics, 15 (1996), 4030).

It is an object of the invention to find a process for preparing metallocenes which has wide applicability and, for example, is also suitable for preparing highly substituted, bulky metallocenes.

It has now surprisingly been found that this object is achieved by use of specific adducts of the formula (I).

The invention accordingly provides a process for preparing a metallocene, which comprises reacting a ligand starting compound with an adduct of the formula (I), $$M^1X_nD_a \qquad (I)$$

where $M^1$ is a metal of group III, IV, V or VI of the Periodic Table of the Elements or an element of the lanthanide or actinide series, preferably titanium, zirconium or hafnium, particularly preferably zirconium, X are identical or different and are each halogen, $C_1$–$C_{10}$-alkoxy, $C_6$–$C_{10}$-aryloxy, $C_1$–$C_{10}$-alkylsulfonate such as mesylate, triflate, nonaflate, $C_6$–$C_{10}$-arylsulfonate such as tosylate, benzenesulfonate, $C_1$–$C_{10}$-alkylcarboxylate such as acetate, formate, oxalate or 1,3-dicarbonylate such as acetylacetonate or fluorinated 1,3-dicarbonylate, in particular chlorine, bromine, particularly preferably chlorine, n is an integer and is 2,3,4, 5 or 6 and corresponds to the oxidation number of the metal $M^1$, a is an integer or fraction and $0<a\leq 4$ and a is preferably in the range from 0.5 to 2.5 and is in particular 1, 1.5 or 2, and D is a linear, cyclic or branched oligoether or polyether containing at least two oxygen atoms or an oligothioether or polythioether containing at least two sulfur atoms, for example dimethoxymethane, diethoxymethane, 1,2-dimethoxyethane, 1,2-diethoxyethane, 1,1,2,2-tetramethoxyethane, pentaerythritol tetramethyl ether, sorbitol hexamethyl ether, diethylene glycol dimethyl ether, diethylene glycol diethyl ether, 1,2,3-propanetriol trimethyl ether, 1,2,3-propanetriol triethyl ether, triethylene glycol dimethy ether, tetraethylene glycol dimethyl ether, pentaethylene glycol dimethyl ether, polyethylene glycol dimethyl ether, 1,3-propanediol dimethyl ether, 1,2-dimethoxycyclohexane, 1,2-dimethoxybenzene, a crown ether such as 18-crown-6, dibenzo-18-crown-6,15-crown-5, 12-crown-4, dimethyl thioglycol, trimethyl thioglycerol, thia-18-crown-6, di(methyl)ethylene thioglycol, in particular 1,2-dimethoxyethane.

Illustrated examples of adducts of the formula (I), which do not, however, restrict the scope of the invention, are:

$ZrCl_4$(1,2-dimethoxyethane)
$ZrCl_4$(dimethyl thioglycol)
$ZrCl_4$(1,2-diethoxyethane)
$ZrCl_4$(1,3-dimethoxypropane)
$ZrCl_4$(1,3-di (methylthio) propane)
$ZrCl_4$(18-crown-6)
$ZrCl_4$(dibenzo-18-crown-6)
$ZrCl_4$(1,2-dimethoxycyclohexane)
$ZrCl_4$(1,2-methoxybenzene)
$ZrCl_4$(diethylene glycol dimethyl ether)
$ZrCl_4$(1,2,3-propanetriol triethyl ether)
$ZrCl_4$(trimethyl thioglycerol)
$ZrCl_4$(triethylene glycol dimethyl ether)
$ZrCl_4$(tetraethylene glycol dimethyl ether)
$ZrCl_4$(O-isopropyl)$_2$ (1,2-dimethoxyethane)
$ZrCl_4$(O-ethyl)$_2$(1,2-dimethoxyethane)
$ZrCl_4$(pentaerythritol tetramethyl ether)
$ZrBr_4$(1,2-dimethoxyethane)
$ZrBr_4$(diethylene glycol dimethyl ether)
$ZrBr_4$(1,2,3-propanetriol triethyl ether)
$ZrBr_4$(triethylene glycol dimethyl ether)
$ZrBr_4$(tetraethylene glycol dimethyl ether)
$Zr(O\text{-isopropyl})_4$(1,2-dimethoxyethane)
$Zr(O\text{-phenyl})_4$(1,2-dimethoxyethane)
$Zr(OEt)_4$(diethylene glycol dimethyl ether)
$Zr(O\text{-tert-butyl})_4$(1,2,3-propanetriol triethyl ether)
$Zr(O\text{-isopropyl})_4$(triethylene glycol dimethyl ether)
$Zr(OMe)_4$(tetraethylene glycol dimethyl ether)
$Zr(OME)_4$(1,2-dimethoxyethane)
$TiCl_4$(1,2-dimethoxyethane)
$TiCl_4$(dimethyl thioglycol)
$TiCl_4$(1,3-dimethoxypropane)
$TiCl_3$(1,2-dimethoxyethane)$_{1.5}$
$TiCl_3$(dimethyl thioglycol)$_{1.5}$
$TiCl_4$(18-crown-6)
$TiCl_3$(18-crown-6)
$TiCl_3$(18-crown-6)$_{1.5}$
$TiCl_4$(dibenzo-18-crown-6)
$TiCl_4$(diethylene glycol dimethyl ether)
$TiCl_3$(diethylene glycol dimethyl ether)$_{1.5}$
$TiCl_4$(sorbitol hexamethyl ether)
$TiCl_3$(sorbitol hexamethyl ether)$_{1.5}$
$Ti(O\text{-isopropyl})_4$(1,2-dimethoxyethane)
$HfCl_4$(1,2-dimethoxyethane)
$HfCl_4$(dimethyl thioglycol)
$HfBr_4$(1,2-dimethoxyethane)
$HfCl_4$(18-crown-6)
$HfBr_4$(18-crown-6)
$Hf(O\text{-isopropyl})_4$(1,2-dimethoxyethane)
$HfCl_4$(diethylene glycol dimethyl ether)
$HfCl_4$(1,2,3-propanetriol triethyl ether)
$HfCl_4$(triethylene glycol dimethyl ether)
$HfCl_4$(tetraethylene glycol dimethyl ether)
$HfCl_4$(diethylene glycol diethyl ether)
$CrCl_3$(1,2-dimethoxyethane)
$CrCl_3$(18-crown-6)
$MoCl_3$(1,2-dimethoxyethane)
$MoCl_4$(1,2-dimethoxyethane)
$MoCl_4$(dibenzo-18-crown-6)

VCl$_3$(1,2-dimethoxyethane)
VCl$_4$(1,2-dimethoxyethane)
VI$_3$(1,2-dimethoxyethane)
VF$_4$(1,2-dimethoxyethane)
NbCl$_4$(1,2-dimethoxyethane)
NbCl$_4$(18-crown-6)
TaCl$_4$(1,2-dimethoxyethane)
TaCl$_4$(18-crown-6)
CeCl$_3$(1,2-dimethoxyethane)
NdCl$_3$(1,2-dimethoxyethane)
ThCl$_4$(1,2-dimethoxyethane)
UCl$_4$(1,2-dimethoxyethane)

Adducts of the formula (I) can be prepared from transition metal compounds of the formula (Ia), $$M^1X_n \quad (Ia)$$

where $M^1$, X and n have the same meanings as in formula (I), by reaction with an oligoether or polyether or an oligothioether or polythioether D in an inert solvent. D is a linear, cyclic or branched oligoether or polyether containing at least two oxygen atoms or an oligothioether or polythioether, containing at least two sulfur atoms, for example dimethoxymethane, diethoxymethane, 1,2-dimethoxyethane, 1,2-diethoxy-ethane, 1,1,2,2-tetramethoxyethane, pentaerythritol tetramethyl ether, sorbitol hexamethyl ether, diethylene glycol dimethyl ether, diethylene glycol diethyl ether, 1,2,3-propanetriol trimethyl ether, 1,2,3-propanetriol triethyl ether, triethylene glycol dimethyl ether, tetraethylene glycol dimethyl ether, pentaethylene glycol dimethyl ether, polyethylene glycol dimethyl ether, 1,3-propanediol dimethyl ether, 1,2-dimethoxycyclohexane, 1,2-dimethoxybenzene, a crown ether such as 18-crown-6, dibenzo-18-crown-6, 15-crown-5, 12-crown-4, dimethyl thioglycol, trimethyl thioglycerol, thia-18-crown-6, di(methylthio)ethylene, in particular 1,2-dimethoxyethane.

The adducts of the formula (I) can be synthesized separately and isolated or can be generated during the process of the invention for preparing the metallocene. The molar ratio of metal $M^1$ to oligoether/polyether or oligothioether/polythioether in this reaction is generally from 100 to 0.01, preferably from 10 to 0.5.

The process of the invention can be used to prepare various types of metallocene, for example bridged or unbridged biscyclopentadienyl complexes as are described, for example, in EP 128 368, EP 561 479, EP 545 304 and EP 576 970, monocyclopentadienyl complexes such as bridged amidocyclopentadienyl complexes as are described, for example, in EP 416 815, multinuclear cyclopentadienyl complexes as described in EP 632 063, π-ligand-substituted tetrahydropentalenes as described in EP 659 758 or π-ligand-substituted tetrahydroindenes as described in EP-661 300.

Preference is given to preparing metallocenes of the formula (II),

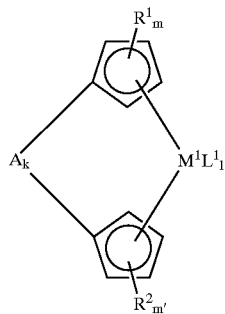

(II)

where $M^1$ is a transition metal of group III, IV, V or VI of the Periodic Table of the Elements or a lanthanide or actinide metal, preferably zirconium, hafnium, titanium, $L^1$ are identical or different and are each a halogen atom, preferably chlorine, a $C_1$–$C_{20}$-group such as a $C_1$–$C_{20}$-alkoxy group or a $C_1$–$C_{20}$-aryloxy group, or $L^1$ can together form a ring system with $M^1$, l is an integer from 1 to 4, preferably 2 or 3, in particular 2, $R^1$ and $R^2$ are identical or different and are each, independently of one another, a hydrogen atom, halogen, a $C_1$–$C_{40}$-group such as $C_1$–$C_{20}$-alkyl, in particular a methyl group, ethyl group, propyl, isopropyl, butyl, sec-butyl, tert-butyl, cyclohexyl, $C_6$–$C_{24}$-aryl which may in turn be substituted, in particular a phenyl or naphthyl group, $C_2$–$C_{24}$-heteroaryl such as pyridyl, furyl, thienyl, pyrimidyl, quinolyl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{18}$-aryloxy, $C_1$–$C_{10}$-haloalkyl, $C_6$–$C_{10}$-haloaryl, $C_2$–$C_{10}$-alkynyl, $C_3$–$C_{20}$-alkylsilyl, such as trimethylsilyl, triethylsilyl, tert-butyldimethylsilyl, triisopropyl-silyl, $C_3$–$C_{20}$-arylsilyl such as triphenylsilyl, or $C_3$–$C_{20}$-alkylarylsilyl such as dimethylphenylsilyl, diphenylmethylsilyl or diphenyl-tert-butylsilyl and $R^1$ and $R^2$ in each case together with the atoms of the cyclopentadienyl ring which connect them may form a monocyclic or polycyclic $C_3$–$C_{25}$ ring system, in particular an indenyl, fluorenyl, benzindenyl or acenaphthindenyl system, which may in turn be substituted, and $R^1$ and $R^2$ in each case together with A may form a ring system, m is 5 when k=0 and m is 4 when k=1,
m' is 5 when k=0 and m' is 4 when k=1,
k is 0 or 1, with the metallocene being unbridged when k=0 and bridged when k=1,
A is a bridge such as

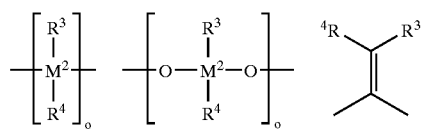

or =BR$^3$, AlR$^3$, —S—, —SO—, —SO$_2$—, =NR$^3$, =PR$^3$, =P(O)R$^3$, o-phenylene, 2,2'-bisphenylene, where $M^2$ is carbon, silicon, germanium, tin, nitrogen or phosphorus, preferably carbon, silicon or germanium, in particular carbon or silicon, and A together with one or more radicals $R^1$ and/or $R^2$ may form a monocyclic or polycyclic ring system, o is 1, 2, 3 or 4, preferably 1 or 2, $R^3$ and $R^4$ are identical or different and are each, independently of one another, a hydrogen atom, halogen, a $C_1$–$C_{20}$-group such as $C_1$–$C_{20}$-alkyl, in particular a methyl group, $C_6$–$C_{14}$-aryl, in particular a phenyl or naphthyl group, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-fluoroalkyl, $C_6$–$C_{10}$-haloaryl, $C_2$–$C_{10}$-alkynyl, $C_3$–$C_{20}$-alkylsilyl, such as trimethylsilyl, triethylsilyl, tert-butyldimethylsilyl, $C_3$–$C_{20}$-arylsilyl, such as triphenylsilyl, or $C_3$–$C_{20}$-alkylarylsilyl such as dimethylphenylsilyl, diphenylsilyl or diphenyl-tert-butylsilyl and $R^3$ and $R^4$ may form a monocyclic or polycyclic ring system.

Illustrated examples of metallocenes, which do not, however, restrict the scope of the invention, are:
dimethylsilanediylbis(indenyl)zirconium dichloride
dimethylsilanediylbis(2-methylindenyl)zirconium dichloride dimethylsilanediylbis(2,4,6-trimethylindenyl)zirconium dichloride
dimethylsilanediylbis(2,5,6-trimethylindenyl)zirconium dichloride
dimethylsilanediylbis[1-(2-methyl-4-phenylindenyl)]zirconium dichloride
dimethylsilanediylbis[1-(2-methylindenyl]zirconium dichloride
dimethylsilanediylbis[1-(2-methyl-4-(1-naphthyl)indenyl)]zirconium dichloride
dimethylsilanediylbis[1-(2-methyl-4-(2-naphthyl)indenyl)]zirconium dichloride
dimethylsilanediylbis[1-(2-methyl-4-mesitylindenyl)]zirconium dichloride
dimethylsilanediylbis[1-(2-methyl-4-(2-methylphenyl)indenyl)]zirconium dichloride
dimethylsilanediylbis[1-(2-methyl-4-(2,3-dimethylphenyl)indenyl)]zirconium dichloride
dimethylsilanediylbis[1-(2-methyl-4-(2,5-dimethylphenyl)indenyl)}zirconium dichloride
dimethylsilanediylbis[1-(2-methyl-4-(2,6-dimethylphenyl)indenyl)]zirconium dichloride
dimethylsilanediylbis[1-(2-methyl-4-(2,3-diethylphenyl)indenyl)]zirconium dichloride
dimethylsilanediylbis[1-(2-methyl-4-(3,5-dimethylphenyl)indenyl)]zirconium dichloride
dimethylsilanediylbis[1-(2-methyl-4-(2-biphenyl)indenyl)]zirconium dichloride
dimethylsilanediylbis[1-(2-methyl-4-(4-diphenyl)indenyl)]zirconium dichloride
dimethylsilanediylbis[1-(2-methyl-4-(3,5-biphenylphenyl)indenyl)]zirconium dichloride
dimethylsilanediylbis[1-(2-methyl-4-(3,5-diisopropylphenyl)indenyl)]zirconium dichloride
dimethylsilanediylbis[1-(2-methyl-4-(2,4,6-trimethoxyphenyl)indenyl)]zirconium dichloride
dimethylsilanediylbis[1-(2-methyl-4-(4-N,N-dimethylaminophenyl)indenyl)] zirconium dichloride
dimethylsilanediylbis[1-(2-methyl-4-(3-N,N-dimethylaminophenyl)indenyl)] zirconium dichloride
dimethylsilanediylbis[1-(2-methyl-4-(2-N,N-dimethylaminophenyl)indenyl)zirconium dichloride
dimethylsilanediylbis[1-(2-methyl-4-(4-trifluoromethylphenyl)indenyl)]zirconium dichloride
dimethylsilanediylbis[1-(2-methyl-4-(3-trifluoromethylphenyl)indenyl)]zirconium dichloride
dimethylsilanediylbis[1-(2-methyl-4-(2-trifluoromethylphenyl)indenyl)]zirconium dichloride
dimethylsilanediylbis[1-(2-methyl-4-(3,5-bis(trifluoromethyl)phenyl)indenyl)] zirconium dichloride
dimethylsilanediylbis[1-(2-methyl-4-(2,4-bis(trifluoromethyl)phenyl)indenyl)]zirconium dichloride
dimethylsilanediylbis[1-(2-methyl-4,5-benzoindenyl)]zirconium dichloride
dimethylsilanediylbis[1-(2-methyl-α-acenaphthindenyl)]zirconium dichloride
dimethylsilanediylbis[1-(2-methyl-4,6-diisopropylindenyl)]zirconium dichloride
dimethylsilanediylbis[1-(2-ethyl-4-phenylindenyl)]zirconium dichloride
dimethylsilanediylbis[1-(2-ethyl-4-naphthylindenyl)]zirconium dichloride
dimethylsilanediylbis[1-(2-isopropyl-4-(phenylindenyl)]zirconium dichloride
dimethylsilanediylbis[1-(2-isopropyl-4-(1-naphthyl)indenyl)]zirconium dichloride
dimethylsilanediylbis[1-(2-isopropyl-4-((2-naphthyl)indenyl)]zirconium dichloride
dimethylsilanediylbis[1-(2-isopropyl-4-(4-methylphenyl)indenyl)]zirconium dichloride
dimethylsilanediylbis[1-(2-isopropyl-4-(3,5-dimethylphenyl)indenyl)]zirconium dichloride
dimethylsilanediylbis[1-(2-isopropyl-4-(4-trifluoromethylphenyl)indenyl)]zirconium dichloride
dimethylsilanediylbis[1-(2-isopropyl-4-(3,5-bis(trifluoromethyl)phenyl)indenyl)]zirconium dichloride
dimethylsilanediylbis[1-(2-isopropyl-4-(4-methoxyphenyl)indenyl)]zirconium dichloride
dimethylsilanediylbis[1-(2-isopropyl-4-(2-furyl)indenyl)]zirconium dichloride
dimethylsilanediylbis[1-(2-cyclohexyl-4-(1-naphthyl)indenyl)]zirconium dichloride
dimethylsilanediylbis[1-(2-cyclohexyl-4-phenylindenyl)]zirconium dichloride
dimethylsilanediylbis[1-(2,4-diphenylindenyl)zirconium dichloride
dimethylsilanediylbis[1-(2,4-dicyclohexylindenyl)]zirconium dichloride
dimethylsilanediylbis[1-(2-methyl-4-phenylindenyl)]hafnium dichloride
dimethylsilanediylbis[1-(2-methyl-4-(1-naphthyl)indenyl)]hafnium dichloride
dimethylsilanediylbis[1-(2-ethyl-4-(naphthyl)indenyl)]hafnium dichloride
dimethylsilanediylbis[1-(2-methyl-4-mesitylindenyl)]hafnium dichloride
dimethylsilanediylbis[1-(2-methyl-4-(2-methylphenyl)indenyl)]hafnium dichloride
dimethylsilanediylbis[1-(2-methyl-4-(2,3-dimethylphenyl)indenyl)]hafnium dichloride
dimethylsilanediylbis[1-(2-cyclohexyl-4-phenylindenyl)]hafnium dichloride
dimethylsilanediylbis(2,3,5-trimethylcyclopentadienyl)zirconium dichloride
dimethylsilanediylbis(2-methyl-4-tert-butylcyclopentadienyl)zirconium dichloride
dimethylsilanediylbis(fluorenyl)zirconium dichloride
methylphenylsilanediylbis[1-(2-methyl-4-phenylindenyl)]zirconium dichloride
methylphenylsilanediylbis[1-(2-methyl-4-naphthylindenyl)]zirconium dichloride
methylphenylsilanediylbis[1-(2-methyl-4-(2,3-dimethylphenyl)indenyl)]zirconium dichloride
diphenylsilanediylbis(1-indenyl)zirconium dichloride
diphenylsilanediylbis[1-(2-methylindenyl)]zirconium dichloride
diphenylsilanediylbis[1-(2-methyl-4-phenylindenyl)zirconium dichloride
diphenylsilanediylbis[1-(2-methyl-4-naphthylindenyl)]zirconium dichloride
diphenylsilanediylbis[1-(2-methyl-4-(2,3-dimethylphenyl)indenyl)]zirconium dichloride
1,2-ethanediylbis[1-(2-methyl-4-phenylindenyl)]zirconium dichloride
1,2-ethanediylbis[1-(2-methyl-4-(1-naphthyl)indenyl)]zirconium dichloride
1,2-ethanediylbis[1-(2-methyl-4-(2,3-dimethylphenyl)indenyl)]zirconium dichloride
1,2-ethanediylbis[1-(2-cyclohexyl-4-phenylindenyl)] zirconium dichloride
1,2-ethanediylbis[1-(2-methyl-4-3,5-bis(trifluoromethyl)phenylindenyl)]zirconium dichloride
1,2-ethanediylbis(fluorenyl)zirconium dichloride 1,2-ethanediylbis(2,3,5-trimethylcyclopentadienyl)zirconium dichloride
1,2-ethanediylbis(2-methyl-4-tert-butylcyclopentadienyl)zirconium dichloride
1,2-ethanediylbis[1-(2-methyl-4-phenylindenyl)]titanium dichloride
1,2-ethanediylbis[1-(2-methyl-4-(1-naphthyl)indenyl)]titanium dichloride
1,2-ethanediylbis(indenyl)]titanium dichloride
1,2-ethanediylbis(tetrahydroindenyl)]titanium dichloride
1,2-butanediylbis[1-(2-methyl-4-phenylindenyl)]zirconium dichloride
1,2-butanediylbis[1-(2-methyl-4-(1-naphthyl)indenyl) zirconium dichloride
1,2-butanediylbis[1-(2-methyl-4-(2-naphthyl)indenyl)]zirconium dichloride
1,2-butanediylbis[1-(2-methyl-4-(3,5-bis(trifluoromethyl)phenylindenyl)]zirconium dichloride
isopropylidenebis[1-(2-methyl-4-phenylindenyl)]zirconium dichloride
isopropylidenebis[1-(2-methyl-4-(2,3-dimethylphenylindenyl)]dimethylzirconium
isopropylidenebis[1-(2-methyl-4-(1-naphthyl)indenyl)]zirconium dichloride
isopropylidenebis[1-(2-cyclohexyl-4-phenyl)indenyl)]zirconium dichloride
isopropylidenebis[1-(2-methyl-4-(3,5-bis(trifluoromethyl)phenylindenyl)]zirconium dichloride
isopropylidenebis(fluorenyl)zirconium dichloride
isopropylidene(indenyl)(fluorenyl)zirconium dichloride
isopropylidene(cyclopentadienyl)(fluorenyl)zirconium dichloride
isopropylidene(cyclopentadienyl)(indenyl)zirconium dichloride
isopropylidenebis(2-methyl-4-tert-butylcyclopentadienyl)zirconium dichloride
bis(cyclopentadienyl)zirconium dichloride
bis(n-butylcyclopentadienyl)zirconium dichloride
bis(1,3-dimethylcyclopentadienyl)zirconium dichloride
bis(pentamethylcyclopentadienyl)zirconium dichloride
bis(indenyl)zirconium dichloride
bis(fluorenyl)zirconium dichloride
bis[2-methyl-4-phenyl)indenyl]zirconium dichloride
bis[2-methyl-4-(2,3-dimethylphenyl)indenyl]zirconium dichloride
bis[2-methyl-4-(1-naphthyl)indenyl]zirconium dichloride
bis[2-methyl-4-mesitylindenyl]zirconium dichloride
bis[2-ethyl-4-(3,5-bis(trifluoromethyl)phenylindenyl]zirconium dichloride
bis[2-cyclohexyl-4-phenylindenyl]zirconium dichloride
[4-($\eta^5$-cyclopentadienyl)-4,6,6-trimethyl($\eta^5$-4,5,6,7-tetrahydropentalenyl)]zirconium dichloride
[4-($\eta^5$-3'-trimethylsilylcyclopentadienyl)-4,6,6-trimethyl($\eta^5$-4,5,6,7-tetrahydropentalenyl)] zirconium dichloride
[4-($\eta^5$-3'-isopropylcyclopentadienyl)-4,6,6-trimethyl($\eta^5$-4,5,6,7-tetrahydropentalenyl)]zirconium dichloride
[4-($\eta^5$-fluorenyl)4-methyl-6-phenyl($\eta^5$-4,5,6,7-tetrahydropentalenyl)]zirconium dichloride
[4-($\eta^5$indenyl)-4-methyl-6-phenyl($\eta^5$-4,5,6,7-tetrahydropentalenyl)]zirconium dichloride
[4-($\eta^5$-cyclopentadienyl)-4,7,7-trimethyl ($\eta^5$-4,5,6,7-tetrahydroindenyl))]zirconium dichloride
[4-($\eta^5$-cyclopentadienyl)-4,7,7-trimethyl($\eta^5$-4,5,6,7-tetrahydroindenyl)]hafnium dichloride
[4-($\eta^5$-cyclopentadienyl)-4,7,7-trimethyl($\eta^5$-4,5,6,7-tetrahydroindenyl)]titanium dichloride
[4-($\eta^5$-3'-tert-butylcyclopentadienyl)-4,7,7-trimethyl($\eta^5$-4,5,6,7-tetrahydroindenyl)]zirconium dichloride
[4-($\eta^5$-3-isopropylcyclopentadienyl)-4,7,7-trimethyl($\eta^5$-4,5,6,7-tetrahydroindenyl)]zirconium dichloride
[4-($\eta^5$-3'-trimethylsilylcyclopentadienyl)-4,7,7-trimethyl ($\eta^5$-4, 5, 6, 7-tetrahydroindenyl)] zirconium dichloride
[4-($\eta^5$-3'-methylcyclopentadienyl)-4,7,7-trimethyl($\eta^5$-4,5,6,7-tetrahydroindenyl)]zirconium dichloride
[4-($\eta^5$-3'-methylcyclopentadienyl)-4,7,7-trimethyl($\eta^5$-4,5,6,7-tetrahydroindenyl)]zirconium dichloride
dimethylsilanediyl(tert-butylamido)(tetramethyl-$\eta^5$-cyclopentadienyl)titanium dichloride
1,2-ethanediyl(tert-butylamido)(tetramethyl-$\eta^5$-cyclopentadienyl)titanium dichloride
dimethylsilanediyl(methylamido)(tetramethyl-$\eta^5$-cyclopentadienyl)titanium dichloride
1,2-ethanediyl(methylamido)(tetramethyl-$\eta^5$-cyclopentadienyl)titanium dichloride
dimethylsilanediyl(tert-butylamido)(2,4-dimethyl-2,4-pentadienyl)titanium dichloride
tetrachloro-[1-(bis($\eta^5$-1H-inden-1-ylidene)methylsilyl-3-$\eta^5$-cyclopenta-2,4-dien-1-ylidene-3-$\eta^5$-9H-fluoren-9-ylidene-)butane]dizirconium.

To prepare metallocenes by the process of the invention, use is made of ligand starting compounds such as cyclopentadiene compounds, for example cyclopentadiene, indene or fluorene derivatives. These can be deprotonated by means of bases and the corresponding anions bind as ligands to transition metals to form metallocenes.

As ligand starting compounds for preparing metallocenes by the process of the invention, preference is given to using compounds of the formula (III),

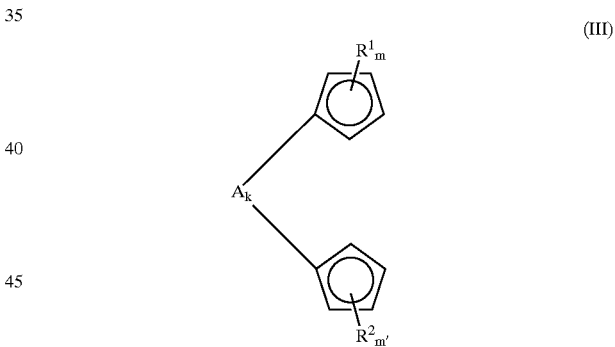

where A, k, $R^1$, $R^2$, m and m' have the same meanings as in formula (II).

Illustrative examples of compounds of the formula (III), which do not, however, restrict the scope of the invention, are:
dimethylbis(indenyl)silane
dimethylbis(2-methylindenyl)silane
dimethylbis(2,4,6-trimethylindenyl)silane
dimethylbis(2,5,6-trimethylindenyl)silane
dimethylbis[1-(2-methyl-4-phenylindenyl)]silane
dimethylbis[1-(2-methylindenyl)]silane
dimethylbis[1-(2-methyl-4-(1-naphthyl)indenyl)]silane
dimethylbis[1-(2-methyl-4-(2-naphthyl)indenyl)]silane
dimethylbis[1-(2-methyl-4-mesitylindenyl)]silane
dimethylbis[1-(2-methyl-4-(2-methylphenyl)indenyl)]silane
dimethylbis[1-(2-methyl-4-(2,3-dimethylphenyl)indenyl)]silane dimethylbis[1-(2-methyl-4-(2,5-dimethylphenyl)indenyl)]silane
dimethylbis[1-(2-methyl-4-(2,6-dimethylphenyl)indenyl)]silane
dimethylbis[1-(2-methyl-4-(2,3-diethylphenyl)indenyl)]silane
dimethylbis[1-(2-methyl-4-(3,5-dimethylphenyl)indenyl)]silane
dimethylbis[1-(2-methyl-4-(2-biphenyl)indenyl)]silane
dimethylbis[1-(2-methyl-4-(4-biphenyl)indenyl)]silane
dimethylbis[1-(2-methyl-4-(3,5-diphenylphenyl)indenyl)]silane
dimethylbis[1-(2-methyl-4-(3,5-diisopropylphenyl)indenyl)]silane
dimethylbis[1-(2-methyl-4-(2,4,6-trimethoxyphenyl)indenyl)]silane
dimethylbis[1-(2-methyl-4-(4-N,N-dimethylaminophenyl)indenyl)] silane
dimethylbis[1-(2-methyl-4-(3-N,N-dimethylaminophenyl)indenyl)] silane
dimethylbis[1-(2-methyl-4-(2-N,N-dimethylaminophenyl)indenyl)] silane
dimethylbis[1-(2-methyl-4-(4-trifluoromethylphenyl)indenyl)]silane
dimethylbis[1-(2-methyl-4-(3-trifluoromethylphenyl)indenyl)]silane
dimethylbis[1-(2-methyl-4-(2-trifluoromethylphenyl)indenyl)]silane
dimethylbis[1-(2-methyl-4-(3,5-bis(trifluoromethyl)phenyl)indenyl)]silane
dimethylbis[1-(2-methyl-4-(2,4-bis(trifluoromethyl)phenyl)indenyl)]silane
dimethylbis[1-(2-methyl-4,5-benzoindenyl)]silane
dimethylbis[1-(2-methyl-α-acenaphthindenyl)]silane
dimethylbis[1-(2-methyl-4,6-diisopropylindenyl)]silane
dimethylbis[1-(2-ethyl-4-phenylindenyl)]silane
dimethylbis[1-(2-ethyl-4-naphthylindenyl)]silane
dimethylbis[1-(2-isopropyl-4-phenylindenyl)]silane
dimethylbis[1-(2-isopropyl-4-(1-naphthyl)indenyl)]silane
dimethylbis[1-(2-isopropyl-4-(2-naphthyl)indenyl)]silane
dimethylbis[1-(2-isopropyl-4-(4-methylphenyl)indenyl)]silane
dimethylbis[1-(2-isopropyl-4-(3,5-dimethylphenyl)indenyl)]silane
dimethylbis[1-(2-isopropyl-4-(4-trifluoromethylphenyl)indenyl)]silane
dimethylbis[1-(2-isopropyl-4-(3,5-bis(trifluoromethyl)phenyl)indenyl)]silane
dimethylbis[1-(2-isopropyl-4-(4-methoxyphenyl)indenyl)]silane
dimethylbis[1-(2-isopropyl-4-(2-furyl)indenyl)]silane
dimethylbis[1-(2-cyclohexyl-4-(1-naphthyl)indenyl)]silane
dimethylbis[1-(2-cyclohexyl-4-phenylindenyl)]silane
dimethylbis[1-(2,4-diphenylindenyl)]silane
dimethylbis[1-(2,4-dicyclohexylindenyl)]silane
dimethylbis[1-(2,3,5-trimethylcyclopentadienyl)silane
dimethylbis[1-(2-methyl-4-tert-butylcyclopentadienyl)silane
dimethylbis(fluorenyl)silane
methylphenylbis[1-(2-methyl-4-phenylindenyl)]silane
methylphenylbis[1-(2-methyl-4-naphthylindenyl)]silane
methylphenylbis[1-(2-methyl-4-(2,3-dimethylphenyl)indenyl)]silane
diphenylbis(1-indenyl)silane
diphenylbis[1-(2-methylindenyl)]silane
diphenylbis[1-(2-methyl-4-phenylindenyl)]silane
diphenylbis[1-(2-methyl-4-naphthylindenyl)]silane
diphenylbis[1-(2-methyl-4-(2,3-dimethylphenyl)indenyl)]silane
1,2-bis[1-(2-methyl-4-phenylindenyl)]ethane
1,2-bis[1-(2-methyl-4-(1-naphthyl)indenyl)]ethane
1,2-bis[1-(2-methyl-4-(2,3-dimethylphenyl)indenyl)]ethane
1,2-bis[1-(2-cyclohexyl-4-phenylindenyl)]ethane
1,2-bis[1-(2-methyl-4-(3,5-bis(trifluoromethyl)phenylindenyl)]ethane
1,2-bis(fluorenyl)ethane
1,2-bis(2,3,5-trimethylcyclopentadienyl)ethane
1,2-bis(2-methyl-4-tert-butylcyclopentadienyl)ethane
1,2-bis[1-(2-methyl-4-phenylindenyl)]butane
1,2-bis[1-(2-methyl-4-(1-naphthyl)indenyl)]butane
1,2-bis[1-(2-methyl-4-(2-naphthyl)indenyl)]butane
1,2-bis[1-(2-methyl-4-(3,5-bis(trifluoromethyl)phenylindenyl)]butane
2,2-bis[1-(2-methyl-4-phenylindenyl)]propane
2,2-bis[1-(2-methyl-4-(2,3-dimethylphenylindenyl)]dimethylzirconium
2,2-bis[1-(2-methyl-4-(1-naphthyl)indenyl)]propane
2,2-bis[1-(2-cyclohexyl-4-phenyl)indenyl)]propane
2,2-bis[1-(2-methyl-4-(3,5-bis(trifluoromethyl)phenylindenyl)]propane
2,2-bis(fluorenyl)propane
2-(indenyl)-2-(fluorenyl)propane
2-(cyclopentadienyl)-2-(fluorenyl)propane
2-(cyclopentadienyl)-2-(indenyl)propane
[4-(cyclopentadienyl)-4,6,6-trimethyl($\eta^5$-4,5,6,7-tetrahydropentalene)]
[4-(3'trimethylsilylcyclopentadienyl)-4,6,6-trimethyl($\eta^5$-4,5,6,7-tetrahydropentalene)
[4-(3'-isopropylcyclopentadienyl)-4,6,6-trimethyl($\eta^5$-4,5,6,7-tetrahydropentalene)
[4-(fluorenyl)-4-methyl-6-phenyl ($\eta^5$-4, 5,6,7-tetrahydropentalene)]
[4-(indenyl)-4-methyl-6-phenyl($\eta^5$-4,5,6,7-tetrahydropentalene)]
[4-(cyclopentadienyl)-4,7,7-trimethyl($\eta^5$-4,5,6,7-tetrahydroindene)]
[4-(3'-tert-butylcyclopentadienyl)-4,7,7-trimethyl-($\eta_5$-4,5,6,7-tetrahydroindene)]
[4-(3-isopropylcyclopentadienyl)-4,7,7-trimethyl ($\eta^5$-4,5,6,7-tetrahydroindene)]
[4-(3'-trimethylsilylcyclopentadienyl)-4,7,7-trimethyl($\eta^5$-4,5,6,7-tetrahydroindene)]
[4-(3'-methylcyclopentadienyl)-4,7,7-trimethyl($\eta^5$-4,5,6,7-tetrahydroindene)]
[4-(3'-methylcyclopentadienyl)-2,4,7,7-tetramethyl ($\eta^5$-4,5,6,7-tetrahydroindene)]
dimethyl(tert-butylamido)(tetramethyl-$\eta^5$-cyclopentadienyl)silane
1-(tert-butylamido)-2-(tetramethyl-$\eta^5$-cyclopentadienyl)ethane
dimethyl(methylamido)(tetramethyl-$\eta^5$-cyclopentadienyl)silane
1-(methylamido)-2-(tetramethyl-$\eta^5$-cyclopentadienyl)ethane
dimethyl(tert-butylamido)-(2,4-dimethyl-2,4-pentadienyl)silane
[1-(bis(1H-inden-1-ylidene)methylsilyl)-3-$\eta^5$-cyclopenta-2,4-dien-1-ylidene)-3-$\eta^5$-9H-fluoren-9-ylidene)butane]

The preparation of metallocenes by the process of the invention is preferably carried out by deprotonation of suitable ligand starting compounds, for example compounds of the formula (III), using bases in an inert solvent or solvent mixture and subsequent reaction with an adduct of the formula (I) which can be prepared separately and used as an isolated compound or alternatively can be generated in situ during the process of the invention.

Preference is given to preparing metallocenes of the formula (II) from ligand starting compounds of the formula (III), as is illustrated in a nonrestrictive way in the following reaction scheme,

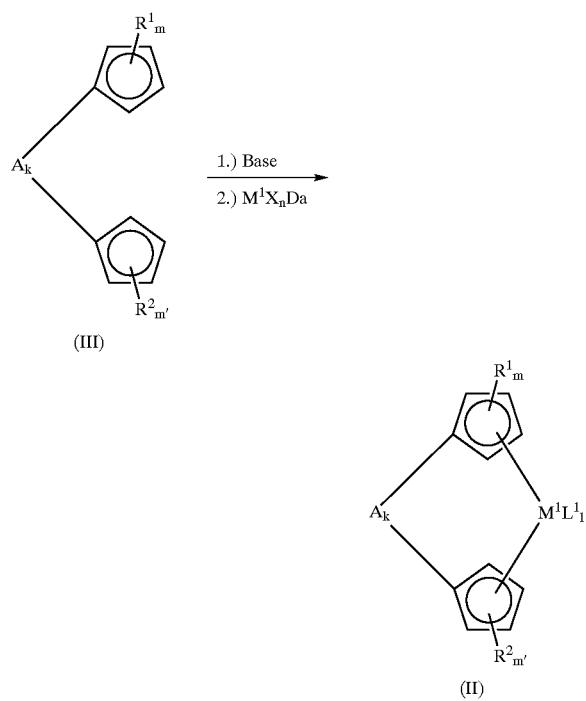

where A, k, $R^1$, $R^2$, m, m', $M^1$, X, n, D, a, $L^1$ and I are defined as in formulae (I) and (II).

Nonrestrictive examples of suitable bases are organolithium compounds such as n-butyllithium, sec-butyllithium, tert-butyllithium, methyllithium, organomagnesium compounds such as dibutylmagnesium, butyloctylmagnesium, Grignard compounds, alkali metal such as sodium, potassium, alkali metal hydrides such as lithium hydride, sodium hydride, potassium hydride or alkali metal amides such as lithium amide, sodium amide, potassium amide, sodium hexamethyl disilazide, potassium hexamethyldisilazide, lithium hexamethyldisilazide, lithium diisopropylamide, lithium diethylamide.

Suitable inert solvents are aliphatic or aromatic hydrocarbons such as toluene, xylene, benzene, mesitylene, pentane, hexane, heptane, cyclohexane, halogenated hydrocarbons such as 1,2-dichloroethane, o-dichlorobenzene, trichloroethylene, dichloromethane, ethers such as diethyl ether, dibutyl ether, methyl tert-butyl ether, anisole, THF, dioxane, 1,2-dimethoxyethane (DME), diglyme and also any mixtures of these.

The process of the invention is generally carried out in a temperature range from −120° C. to +300° C., preferably in a temperature range from −78° C. to +150° C., particularly preferably at a temperature in the range from 0° C. to 120° C.

The molar ratio of the above-described suitable bases to ligand starting compounds, for example compounds of the formula (III), is generally in the range from 10 to 0.1, preferably from 4 to 0.5, particularly preferably from 3 to 0.8, in the process of the invention.

The molar ratio of adducts of the formula (I) to ligand starting compounds, for example compounds of the formula (III), is generally in the range from 100 to 0.01, preferably from 10 to 0.1, in the process of the invention.

The concentration of the ligand starting compounds in the reaction mixture is generally in the range from 0.0001 mol/l to 8 mol/l, preferably in the range from 0.01 mol/l to 3 mol/l, particularly preferably in the range from 0.1 mol/l to 2 mol/l.

The adducts of the formula (I) can be formed under the reaction conditions and reacted further without isolation. Preference is given to preparing the adducts of the formula (I) separately and using them as isolated compounds in the process of the invention.

The reaction time is generally in the range from 5 minutes to 1 week, preferably in the range from 15 minutes to 48 hours.

The metallocenes which can be prepared by the process of the invention are highly active catalyst components for olefin polymerization. Depending on the substitution pattern of the ligands, the metallocenes can be obtained as a mixture of isomers. For the polymerization, the metallocenes are preferably used in isomerically pure form. The use of the racemate is in most cases sufficient.

However, it is also possible to use the pure enantiomer in the (+) or (−) form. Use of the pure enantiomers enables an optically active polymer to be prepared. However, the configurational isomers of the metallocenes should be separated, since the polymerization-active center (the metal atom) in these compounds usually produces a polymer having different properties. For certain applications, for example soft moldings, this can be thoroughly desirable.

The metallocenes obtained in the process of the invention, in particular metallocenes of the formula (II), are suitable for preparing a polyolefin by polymerization of at least one olefin in the presence of a catalyst comprising at least one cocatalyst and at least one metallocene. For the purposes of the present invention, the term polymerization encompasses both homopolymerization and copolymerization.

The metallocenes prepared in the process of the invention, in particular metallocenes of the formula (II), can be used for the polymerization of one or more olefins of the formula $R^\alpha$—CH=CH—$R^\beta$, where $R^\alpha$ and $R^\beta$ are identical or different and are each a hydrogen atom or a hydrocarbon radical having from 1 to 20 carbon atoms, in particular from 1 to 10 carbon atoms, and $R^\alpha$ and $R^\beta$ together with the atoms connecting them can form one or more rings. Examples of such olefins are 1-olefins having from 2 to 40, preferably 2–10, carbon atoms, e.g. ethylene, propylene, 1-butene, 1-pentene, 1-hexene, 4-methyl-1-pentene or 1-octene, styrene, dienes such as 1,3-butadiene, isoprene, 1,4-hexadiene or cyclic olefins such as norbornene or ethylidenenorbornene.

Preference is given to homopolymerizing ethylene or propylene or copolymerizing ethylene with one or more cyclic olefins such as norbornene and/or one or more acyclic 1-olefins having from 3 to 20 carbon atoms, e.g. propylene and/or one or more dienes having from 4 to 20 carbon atoms, e.g. 1,3-butadiene or 1,4-hexadiene. Examples of such copolymers are ethylene-norbornene copolymers, ethylene-propylene copolymers and ethylene-propylene-1,4-hexadiene copolymers.

The polymerization is preferably carried out at a temperature of from −60 to 250° C., particularly preferably from 50 to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. A preferred embodiment is gas-phase and solution polymerization.

The catalyst used preferably comprises one metallocene compound. It is also possible to use two or more metallocene compounds, e.g. to prepare polyolefins having a broad or multimodel molar mass distribution.

In principle, suitable cocatalysts are all compounds which, owing to their Lewis acidity, can convert the uncharged metallocene into a cation and stabilize the latter ("labile coordination"). Furthermore, the catalyst or the anion formed therefrom should undergo no further reactions with the metallocenium cation (EP 427 697). The cocatalyst used is preferably an aluminum compound and/or a boron compound.

The boron compound preferably has the formula $R^a{}_x NH_{4-x}BR^b{}_x$, $R^a{}_x PH_{4-x}BR^b{}_4$, $R^a{}_3 CBR^b{}_4$ or $BR^b{}_3$, where x is from 1 to 4, preferably 3, the radicals $R^a$ are identical or different, preferably identical, and are $C_1$–$C_{10}$-alkyl or $C_6$–$C_{18}$-aryl or two radicals $R^a$ together with the atoms connecting them form a ring and the radicals $R^b$ are identical or different, preferably identical, and are $C_6$–$C_{18}$-aryl which may be substituted by alkyl, haloalkyl or fluorine. In particular, $R^a$ is ethyl, propyl, butyl or phenyl and Rb is phenyl, pentafluorophenyl, 3,5-bis(trifluoromethyl)phenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula C for the linear type and/or the formula D for the cyclic type,

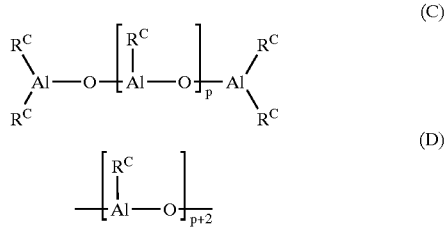

(C)

(D)

where, in the formulae C and D, the radicals $R^c$ are identical or different and are each hydrogen or a $C_1$–$C_{20}$-hydrocarbon group such as a $C_1$–$C_{18}$-alkyl group, a $C_6$–$C_{18}$-aryl group or benzyl and p is an integer from 2 to 50, preferably from 10 to 35.

The radicals $R^c$ are preferably identical and are hydrogen, methyl, isobutyl, phenyl or benzyl, particularly preferably methyl. If the radicals $R^c$ are different, they are preferably methyl and hydrogen or alternatively methyl and isobutyl, with hydrogen or isobutyl preferably being present in a numerical proportion of from 0.01 to 40% (of the radicals $R^c$).

The methods of preparing the aluminoxanes are known. The precise spatial structure of the aluminoxanes is not known (J. Am. Chem. Soc. (1993) 155, 4971). For example, it is conceivable that chains and rings are connected to form larger two-dimensional or three-dimensional structures.

Regardless of the method of preparation, all aluminoxane solutions have in common a variable content of unreacted aluminum starting compound which is present in free form or as adduct.

Before use in the polymerization reaction, it is possible to preactivate the metallocene compound using a cocatalyst, in particular an aluminoxane. This significantly increases the polymerization activity. The preactivation of the metallocene compound is preferably carried out in solution. Here, the metallocene compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of from $10^{-4}$ to 1 mol per mol of aluminoxane. The preactivation time is from 5 minutes to 60 hours, preferably from 5 to 60 minutes. The preactivation is preferably carried out at a temperature of from −78° to 100° C., preferably from 10° to 80° C.

The metallocene compound is preferably employed in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is preferably used in a concentration of from $10^{-6}$ to $10^{-1}$ mol, preferably from $10^{-5}$ to $10^{-2}$ mol, per $dm^3$ of solvent or per $dm^3$ of reactor volume. The other cocatalysts mentioned are used in approximately equimolar amounts to the metallocene compound. However, higher concentrations are also possible in principle.

The aluminoxane can be prepared in various ways by known methods. One of the methods is, for example, to react an aluminum hydrocarbon compound and/or a hydride aluminum hydrocarbon compound with water (gaseous, solid, liquid or bound—for example as water of crystallization) in an inert solvent (for example toluene). An aluminoxane having different radicals $R^c$ is prepared, for example, by reacting two different trialkylaluminums corresponding to the desired composition with water.

To remove catalyst poisons present in the olefin, purification using an aluminum compound, preferably an aluminum alkyl such as trimethylaluminum or triethylaluminum, is advantageous. This purification can be carried out either in the polymerization system itself or the olefin is brought into contact with the aluminum compound and subsequently separated off again before being introduced into the polymerization system.

As molar mass regulator and/or to increase the catalyst activity, hydrogen can be added in the process of the invention. This enables low molecular weight polyolefins such as waxes to be obtained.

The metallocene compound is preferably reacted with the cocatalyst outside the polymerization reactor in a separate step using a suitable solvent. Application to a support can be carried out during this step.

In the process for preparing a polyolefin, a prepolymerization can be carried out with the aid of the metallocene compound. The prepolymerization is preferably carried out using the (or one of the) olefin(s) used in the polymerization.

The catalyst used can be supported. Application to a support enables, for example, the particle morphology of the polyolefin prepared to be controlled. Here, the metallocene compound can be reacted first with the support and subsequently with the cocatalyst. It is also possible to apply the cocatalyst to a support first and subsequently react it with the metallocene compound. Another possibility is to apply the reaction product of metallocene compound and cocatalyst to a support. Suitable support materials are, for example, silica gels, aluminum oxides, solid aluminoxane or other inorganic support materials such as magnesium chloride. Another suitable support materials is a polyolefin powder in finely divided form. The preparation of the supported cocatalyst can be carried out, for example, as described in EP 567 952.

Preferably, the cocatalyst, e.g. aluminoxane, is applied to a support such as silica gel, aluminum oxide, solid aluminoxane, another inorganic support material or a polyolefin powder in finely divided form and then reacted with the metallocene.

As inorganic supports, it is possible to use oxides which have been produced flame-pyrolytically by combustion of element halides in a hydrogen/oxygen flame or can be prepared as silica gels in particular particle size distributions and particle shapes.

The preparation of the supported cocatalyst can be carried out, for example, as described in EP 578 838 in the following manner in a stainless steel reactor of explosion-protected design having a pumped circulation system rated at 60 bar, with inert gas supply, temperature control by means of jacket cooling and a second cooling circuit via a heat exchanger in the pumped circulation system. The pumped circulation system draws in the reactor contents via a connection in the bottom of the reactor by means of a pump and pushes it into a mixer and through a riser line via a heat exchanger back into the reactor. The mixer is configured so that the inlet has a constricted pipe cross section in which an increased flow velocity results and into whose turbulence zone there is inserted, axially and counter to the flow direction, a thin feed line through which, pulsed, a defined amount of water can be fed in under 40 bar of argon. The reaction is monitored via a sampler on the pumped circuit.

However, other reactors are also suitable in principle.

The above-described reactor having a volume of 16 dm$^3$ is charged with 5 dm$^3$ of decane under inert conditions. 0.5 dm$^3$ (=5.2 mol) of trimethylaluminum are added at 25° C. 250 g of silica gel SD 3216-30 (Grace AG) which have been dried beforehand at 120° C. in an argon-fluidized bed are then introduced into the reactor via a solids funnel and homogeneously distributed by means of the stirrer and the pumped circulation system. A total amount of 76.5 g of water is introduced into the reactor in portions of 0.1 cm$^3$ every 15 seconds over a period of 3.25 hours. The pressure, which is due to argon and the gases evolved, is kept constant at 10 bar by means of a pressure regulating valve. After all the water has been introduced, the pumped circulation system is switched off and stirring is continued for another 5 hours at 25° C.

The supported catalyst prepared in this way is used as a 10% suspension in n-decane. The aluminum content is 1.06 mmol of Al per cm$^3$ of suspension. The isolated solid contains 31% by weight of aluminum and the suspension medium contains 0.1% by weight of aluminum.

Further possible ways of preparing a supported cocatalyst are described in EP 578 838.

The metallocene prepared according to the invention is then applied to the supported cocatalyst by stirring the dissolved metallocene with the supported cocatalyst. The solvent is removed and replaced by a hydrocarbon in which both cocatalyst and metallocene are insoluble.

The reaction to form the supported catalyst system is carried out at a temperature of from −20 to +120° C., preferably from 0 to 100° C., particularly preferably from 15 to 40° C. The metallocene is reacted with the supported cocatalyst by combining a 1–40% by weight suspension, preferably a 5–20% by weight suspension, of the cocatalyst in an aliphatic, inert suspension medium such as n-decane, hexane, heptane or diesel oil with a solution of the metallocene in an inert solvent such as toluene, hexane, heptane or dichloromethane or with the finely milled solid metallocene. Conversely, a solution of the metallocene can also be reacted with the solid cocatalyst.

The reaction is carried out by intensive mixing, for example by stirring, at a molar Al/M$^1$ ratio of from 100/1 to 10,000/1, preferably from 100/1 to 3000/1, and a reaction time of from 5 to 120 minutes, preferably from 10 to 60 minutes, particularly preferably from 10 to 30 minutes, under inert conditions.

During the reaction time for preparing the supported catalyst system, particularly when using metallocenes according to the invention having absorption maxima in the visible region, changes in the color of the reaction mixture occur and enable the progress of the reaction to be followed.

After the reaction time has elapsed, the supernatant solution is separated off, for example by filtration or decantation. The solid which remains is washed from 1 to 5 times with an inert suspension medium such as toluene, n-decane, hexane, diesel oil or dichloromethane to remove soluble constituents in the catalyst formed, in particular to remove unreacted and therefore soluble metallocene.

The supported catalyst system prepared in this way can be resuspended as a vacuum-dried powder or while still moist with solvent and be metered as suspension in one of the abovementioned inert suspension media into the polymerization system.

If the polymerization is carried out as a suspension or solution polymerization, use is made of an inert solvent customary for the Ziegler low-pressure process. For example, the polymerization is carried out in an aliphatic or cycloaliphatic hydrocarbon, for example propane, butane, hexane, heptane, isooctane, cyclohexane or methylcyclohexane. It is also possible to use a petroleum fraction or hydrogenated diesel oil fraction. Toluene can also be used. Preference is given to carrying out the polymerization in the liquid monomer.

Before addition of the catalyst, in particular the supported catalyst system (comprising the metallocene prepared according to the invention and a supported cocatalyst), another aluminum alkyl compound such as trimethylaluminum, triethylaluminum, triisobutylaluminum, trioctylaluminum or isoprenylaluminum can be additionally introduced into the reactor to make the polymerization system inert (for example to remove catalyst poisons present in the olefin). This compound is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This makes it possible to select a small molar Al/M$^1$ ratio in the synthesis of a supported catalyst system. If inert solvents are used, the monomers are metered in gaseous or liquid form.

The process of the invention makes it possible to prepare metallocenes in high yield using the adducts of the formula (I) and also enables new metallocenes to be obtained. The process of the invention also has a wide applicability so that a variety of structurally different types of metallocene can be synthesized, in particular bulky compounds.

The invention is illustrated by the following examples which do not, however, restrict the invention.

General procedures: Preparation and handling of the compounds were carried out with exclusion of air and moisture under argon (Schlenk technique). All solvents required were freed of water and oxygen before use by boiling for a number of hours over suitable desiccants and subsequent distillation under argon.

EXAMPLE 1

Zirconium tetrachloride-(1,2-dimethoxyethane) adduct

A suspension of 18.5 g (80 mmol) of zirconium tetrachloride in 250 ml of dichloromethane is admixed at room temperature with 7.2 g (80 mmol) of 1,2-dimethoxyethane and stirred at this temperature for 1 hour. The mixture is subsequently filtered and the filtrate is admixed at −30° C. with 100 ml of pentane and stored at this temperature for 5 hours. The residue is filtered off, washed with pentane and dried under reduced pressure.

This gives 22 g (85%) of zirconium tetrachloride-(1,2-dimethoxyethane) adduct.

Example 1a

Hafnium tetrachloride-(1,2-dimethoxyethane) adduct

The corresponding hafnium tetrachloride-(1,2-dimethoxyethane) adduct is prepared using a method analogous to Example 1.

Example 1b

Zirconium tetrachloride-(1,2-S,S-dimethyl thioglycol) adduct

The corresponding zirconium tetrachloride-(1,2-S,S-dimethyl thioglycol) adduct is prepared by a method analogous to Example 1 using 1,2-S,S-dimethyl thioglycol.

Example 1c

Titanium tetrachloride-DME adduct

A solution of 19 g (100 mmol) of titanium tetrachloride in 250 ml of dichloromethane is admixed at 0° C. with 9.0 g (100 mmol) of 1,2-dimethoxyethane and stirred at room temperature for another 1 hour. The solvent is subsequently taken off, giving 24 g (86%) of titanium tetrachloride-(1,2-dimethoxyethane) adduct as a yellow solid.

EXAMPLE 2

Dimethylsilanediylbis(2-methyl-4-(2-methylphenyl)indenyl)zirconium dichloride

A solution of 1 g (2 mmol) of dimethylbis(2-methyl-4-(2-methylphenyl)indenyl)silane in 20 ml of toluene and 1 ml of THF is admixed with 1.5 ml (4 mmol) of a 2.66 molar solution of n-BuLi in toluene and the mixture is stirred for another 2 hours at 80° C. After deprotonation is complete, the mixture is allowed to cool to 40° C., 0.65 g (2 mmol) of zirconium tetrachloride-(1,2-dimethoxyethane) adduct is added and the mixture is stirred for another 2 hours at this temperature. The solvent is then removed and the residue is extracted with 100 ml of dichloromethane. Taking off the dichloromethane leaves the crude complex which is purified further by recrystallization from toluene. This gives 850 mg (65%) of the pure metallocene (rac/meso 1:1).

$^1$H-NMR (300 MHz, CDCl$_3$): 7.58–6.90 (m, 16H), 2.49–2.20 (m, 12H), 1.51–1.27 (m, 6H).

EXAMPLE 3

Dimethylsilanediylbis(2-methyl-4-(2,3-dimethylphenyl)indenyl)zirconium dichloride The synthesis of dimethylsilanediylbis(2-methyl-4-(2,3-dimethylphenyl)indenyl)zirconium dichloride was carried out by a method similar to Example 2 using the zirconium tetrachloride-(1,2-dimethoxyethane) adduct and the complex was isolated in a yield of 61%.

$^1$H-NMR (300 MHz, CDCl$_3$): 7.58–6.8 (m, 14H), 2.48–2.22 (m, 18H), 1.50–1.25 (m, 6H).

EXAMPLE 4

Dimethylsilanediylbis(2-cyclohexyl-4-phenylindenyl)zirconium dichloride

The synthesis of dimethylsilanediylbis(2-cyclohexyl-4-phenylindenyl)zirconium dichloride was carried out by a method similar to Example 2 using the zirconium tetrachloride-1(1,2-dimethoxyethane) adduct. The complex was isolated in a yield of 59%.

$^1$H-NMR (300 MHz, CDCl$_3$): 7.65–7.06 (m, 16H), 6.92 (s, 2H), 2.88–2.75 (m, 2H), 2.00–0.95 (m, 20H), 1.49–1.28 (m, 6H).

Example 4a

Dimethylsilanediylbis(2-cyclohexyl-4-phenylindenyl)zirconium dichloride

The synthesis of dimethylsilanediylbis(2-cyclohexyl-4-phenylindenyl)zirconium dichloride was carried out by a method similar to Example 2 using the analogous zirconium tetrachloride-(1,2-S,S-dimethylthioglycol) adduct. The complex was isolated in a yield of 49%.

$^1$H-NMR (300 MHz, CDCl$_3$): 7.65–7.06 (m, 16H), 6.92 (s, 2H), 2.88–2.75 (m, 2H), 2.00–0.95 (m, 20H), 1.49–1.28 (m, 6H).

Comparative Example to Example 4

Dimethylsilanediylbis(2-cyclohexyl-4-phenylindenyl)zirconium dichloride

In a comparative experiment, the procedure of Example 4 was repeated using zirconium tetrachloride in place of the zirconium tetrachloride-(1,2-dimethoxyethane) adduct. In this case, no complex could be isolated.

EXAMPLE 5

Dimethylsilanediylbis(2-cyclohexyl-4-phenylindenyl)hafnium dichloride

The synthesis of dimethylsilanediylbis(2-cyclohexyl-4-phenylindenyl)hafnium dichloride was carried out by a method similar to Example 2 using the analogous hafnium tetrachloride-(1,2-dimethoxyethane) adduct. The complex was isolated in a yield of 60%.

$^1$H-NMR (300 MHz, CDCl$_3$): 7.67–7.01 (m, 16H), 6.92 (s, 2H), 2.88–2.75 (m, 2H), 2.00–0.94 (m, 20H), 1.45–1.25 (m, 6H).

EXAMPLE 6

Dimethylsilanediylbis(2-methyl-4-(2,4,6-trimethylphenyl)indenyl)zirconium dichloride The synthesis of dimethylsilanediylbis(2-methyl-4-(2,4,6-trimethylphenyl)indenyl)zirconium dichloride was carried out by a method similar to Example 2 using the zirconium tetrachloride-(1,2-dimethoxyethane) adduct. The complex was isolated in a yield of 50%.

$^1$H-NMR (300 MHz, CDCl$_3$): 7.55.6.82 (m, 12H), 2.47–2.23 (m, 24H), 1.51–1.26 (m, 6H).

EXAMPLE 7

Dimethylsilanediylbis(2,4-diphenylindenyl)zirconium dichloride

The synthesis of dimethylsilanediylbis(2,4-diphenylindenyl)zirconium dichloride was carried out by a method similar to Example 2 using the zirconium tetrachloride-(1,2-dimethoxyethane) adduct. The complex was isolated in a yield of 57%.

$^1$H-NMR (300 MHz, CDCl$_3$): 7.81–6.91 (m, 26H, 6.75/6.69 (s, 2H), 1.45/0.41 (d, 6H, meso) 0.87 (s, 6H, rac).

EXAMPLE 8

Dimethylsilanediylbis(2-isopropyl-4-phenylindenyl) zirconium dichloride

The synthesis of dimethylsilanediylbis(2-isopropyl-4-phenylindenyl)zirconium dichloride was carried out by a method similar to Example 2 using the zirconium tetrachloride-(1,2-dimethoxyethane) adduct. The complex was isolated in a yield of 51%.

$^1$H-NMR (300 MHz, CDCl$_3$): 7.70–7.03 (m, 18H), 3.20 (sept., 2H), 1.41 (s, 6H), 1.13 (m, 12H).

EXAMPLE 9

Dimethylsilanediyl(tert-butylamido)tetramethyl-$\eta^5$-cyclopentadienyl)titanium dichloride The synthesis of dimethylsilanediyl(tert-butylamido) (tetramethyl-$\eta^5$-cyclopentadienyl) titanium dichloride was carried out by a method similar to Example 2 using the titanium tetrachloride-(1,2-dimethoxyethane) adduct. The complex was isolated in a yield of 61%.

$^1$H-NMR (300 MHz, CDCl$_3$): 2.06 (s, 6H), 1.94 (s, 6H), 1.58 (s, 9H), 0.30 (s, 6H).

Example 9a

Dimethylsilanediyl(tert-butylamido)(tetramethyl-$\eta^5$-cyclopentadienyl)titanium dichloride A solution of 1 g (3.98 mmol) of dimethyl(tert-butylamido)(tetramethylcyclopentadienyl) silane in 45 ml of THF is admixed at 0° C. with 2.98 ml (8 mmol) of n-butyllithium (2.68 molar in toluene) and the mixture is stirred for 1 hour at room temperature. This is subsequently added to a cooled (−78° C.) solution of 1.15 g (3.98 mmol) of titanium trichloride-1,2-dimethoxyethane adduct (TiCl$_3$*1.5DME) in 45 ml of THF and the resulting reaction mixture is slowly warmed to room temperature. After addition of 1.1 g (3.98 mmol) of lead(II) chloride, the suspension is stirred for another 12 hours. The solvent mixture is then removed under reduced pressure, the residue is taken up in dichloromethane and filtered through Celite. The filtrate is finally evaporated and admixed with pentane, as a result of which the product precipitates in the freezer. After removal of the mother liquor, 0.85 g (59%) of the complex is isolated.

EXAMPLE 10

Dimethylsilanediylbis(2-methyl-4-phenylindenyl) titanium dichloride

The synthesis of dimethylsilanediylbis(2-methyl-4-phenylindenyl)titanium dichloride was carried out by a method similar to Example 2 using the titanium tetrachloride-(1,2-dimethoxyethane) adduct. The complex was isolated in a yield of 47%.

$^1$H-NMR (300 MHz, CDCl$_3$): 7.89–6.95 (m, 18H), 2.61/2.40 (s, 6H), 1.45 (d, 6H, meso), 1.41 (s, 6H, rac).

EXAMPLE 11

[4-($\eta^5$-fluorenyl)-4-methyl-6-phenyl-($\eta^5$-4,5,6,7-tetrahydropentalenyl)]zirconium dichloride 4.7 ml (12.6 mmol) of n-butyllithium, 20% in toluene, are added dropwise at room temperature to 2.16 g (6 mmol) of 1-fluorenyl-3-phenyl-1-methyl-1,2,3-trihydropentalene in 50 ml of toluene. After stirring for 4 hours at 60° C., the mixture is cooled to 10° C. 1.94 g (6 mmol) of zirconium tetrachloride-(1,2-dimethoxyethane) adduct are added to the red suspension obtained in this way and the mixture is stirred for 3 hours at room temperature. After filtration through Celite, the filter is washed twice with 50 ml each time of hot (80° C.) toluene. Evaporation of the combined filtrates to 10 ml, cooling to −30° C., filtration of the precipitated red powder and drying gives 0.970 g (1.9 mmol) of the complex (31%).

$^1$H-NMR (300 MHz, CDCl$_3$): 7.99–7.75, 7.52–6.93 (13H, m. arom. protons), 6.32 (1H, dd, arom. Cp—H), 6.16 (1 H, t, arom. Cp proton), 4.45 (1 H, dd, CH$_2$), 4.17 (1 H, dd, CH2), 3.03 (1 H, dd, CH—Ph), 2.45 (3 H, s, CH$_3$)

EXAMPLE 12

Dimethylsilanediylbis(2,3,5-trimethylcyclopentadienyl) zirconium dichloride

A solution of 3 g (11 mmol) of dimethylsilanediylbis(2,3,5-trimethylcyclopentadienyl) silane in 20 ml of toluene and 1 ml of THF is admixed with 8.22 ml (22 mmol) of a 2.68 molar solution of n-BuLi in toluene and the mixture is stirred for 2 hours at 80° C. After cooling to 45° C., 3.91 g (12.1 mmol) of zirconium tetrachloride-(1,2-dimethoxyethane) adduct are added thereto and the mixture is stirred at 60° C. for 2 hours. The solvent is removed and the residue is extracted with 125 ml of toluene. Taking off the toluene gives 2.85 g (60%) of the pure metallocene (pseudo-rac/pseudo-meso 1:1).

$^1$H-NMR (300 MHz, CDCl$_3$): 6.50 (s, 1H), 6.38 (s, 1H), 2.25 (s, 3H), 2.20 (s, 3H), 2.16 (s, 3H), 2.12 (s, 3H), 1.98 (s, 3H), 1.88 (s, 3H), 0.98/094 (s, 6H), 0.95 (s, 6H).

What is claimed is:

1. A process for preparing a metallocene, which comprises reacting a ligand starting compound with an adduct of the formula (I), $$M^1X_nD_a \quad (I)$$

wherein $M^1$ is a metal of group III, V or VI of the Periodic Table of the Elements or an element of the Lanthanide or actinides series and n is 2, 3, 4, 5 or 6 and corresponds to the oxidation number of the metal $M^1$ or where $M^1$ is a metal of group IV of the Periodic Table of the Elements and n is 4, and X are identical or different are each halogen, $C_1$–$C_{10}$-alkoxy-, $C_8$–$C_{10}$-aryloxy, $C_1$–$C_{10}$-alkylsulfonate, $C_1$–$C_{10}$-alkylcarboxylate, or 1,3-dicarbonylate, a is an integer or fraction and $0<a\leqq 4$ and D is a linear, cyclic or branched oligoether or polyether containing at least two oxygen atoms or an oligothioether or polythioether containing at least two sulfur atoms.

2. The process as claimed in claim 1, wherein the ligand starting compound is deprotonated using a base.

3. The process as claimed in claim 1, wherein $M^1$ is titanium, zirconium or hafnium.

4. The process as claimed in claim 1, wherein the metallocene is a bridged or unbridged biscyclopentadienyl complex, a monocyclopenrtadienyl complex, a multinuclear monocyclopenrtadienyl complex, a tetrahydropentalene complex or a tetrahydroindene complex.

5. The process as claimed in claim 1, wherein D is 1,2-dimethoxyethane.

6. A method which comprises:
(i) reacting an alkali salt of a compound of Formula I

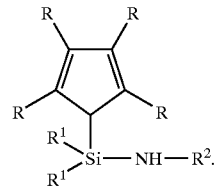

with a slurry of a TiCl$_4$.DME adduct in a non-interfering medium wherein a reaction mixture containing a compound of Formula II

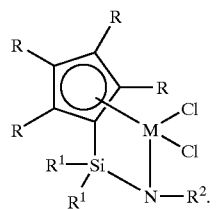

is produced.

7. The method of claim 6 wherein said alkali metal salt is a lithium salt.

8. The method of claim 6 wherein said non-interfering medium is a hydrocarbon medium.

9. The method of claim 6 wherein said non-interfering medium is Isopar E, or hexanes, or a mixture of Isopar E and diethyl ether, or a mixture of hexanes and diethyl ether.

10. The method of claim 6 conducted at a temperature of −20° C. to 0° C.

* * * * *